United States Patent [19]
Namey, Jr.

[11] Patent Number: 5,902,276
[45] Date of Patent: May 11, 1999

[54] TWO-SHOT MOLDED PLUNGER

[75] Inventor: David Namey, Jr., Pittsburgh, Pa.

[73] Assignee: Liebel-Flarsheim Company, Cincinnati, Ohio

[21] Appl. No.: 08/756,803

[22] Filed: Nov. 26, 1996

[51] Int. Cl.⁶ .................................................. A61M 5/315
[52] U.S. Cl. ............................................................ 604/218
[58] Field of Search .................................. 604/222, 230, 604/218

[56] References Cited

U.S. PATENT DOCUMENTS

| | | |
|---|---|---|
| 2,333,059 | 10/1943 | Tucker . |
| 2,337,550 | 12/1943 | Crosby . |
| 3,178,497 | 4/1965 | Moscicki . |
| 3,221,373 | 12/1965 | Kwan . |
| 3,890,956 | 6/1975 | Moorehead .............................. 604/222 |
| 4,201,209 | 5/1980 | LeVeen et al. ........................ 128/218 P |
| 4,214,507 | 7/1980 | Hock et al. ................................ 92/254 |
| 4,340,067 | 7/1982 | Rattenborg .............................. 604/222 |
| 4,874,372 | 10/1989 | McArthur et al. ...................... 604/110 |
| 5,397,313 | 3/1995 | Gross ....................................... 604/218 |

*Primary Examiner*—Wynn Wood Coggins
*Assistant Examiner*—Deborah Blyveis
*Attorney, Agent, or Firm*—Wood,Herron & Evans,L.L.P.

[57] ABSTRACT

A syringe plunger is formed by a two-shot molding process. A hard plastic core is formed in a first mold, and the distal portion of the hard plastic core is subsequently overmolded with soft rubber. The result is a fully automated manufacturing process increasing quality and lowering costs, and a unique plunger having a hard plastic core and soft rubber exterior which are molecularly and permanently bonded together.

16 Claims, 6 Drawing Sheets

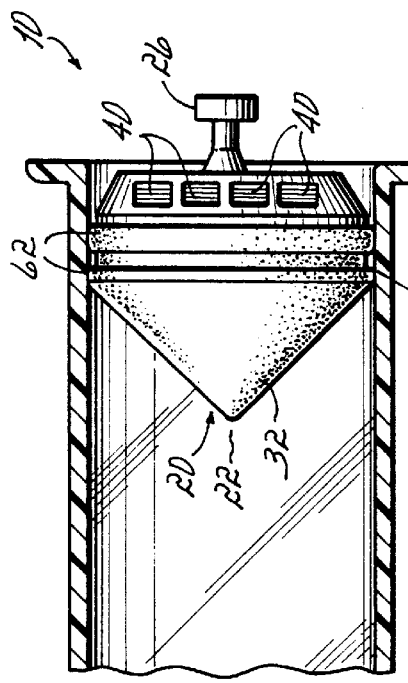
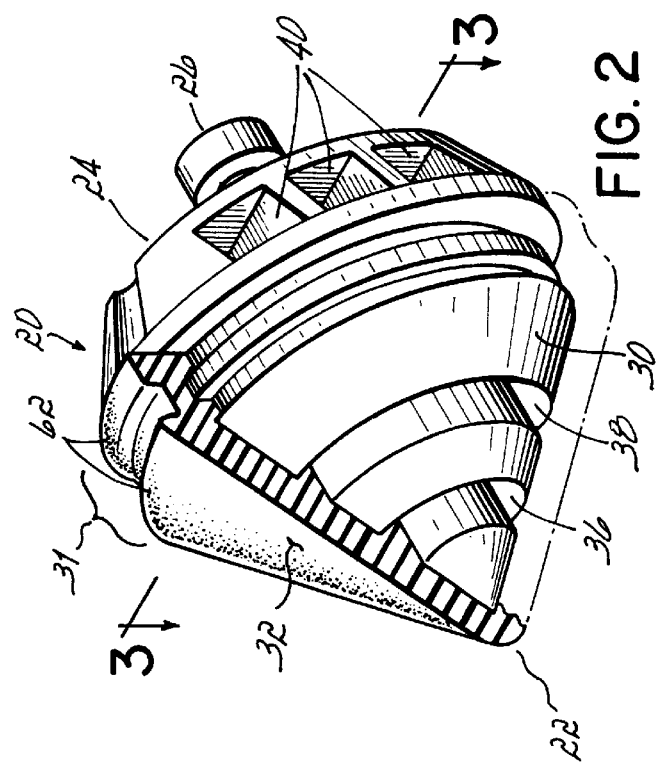
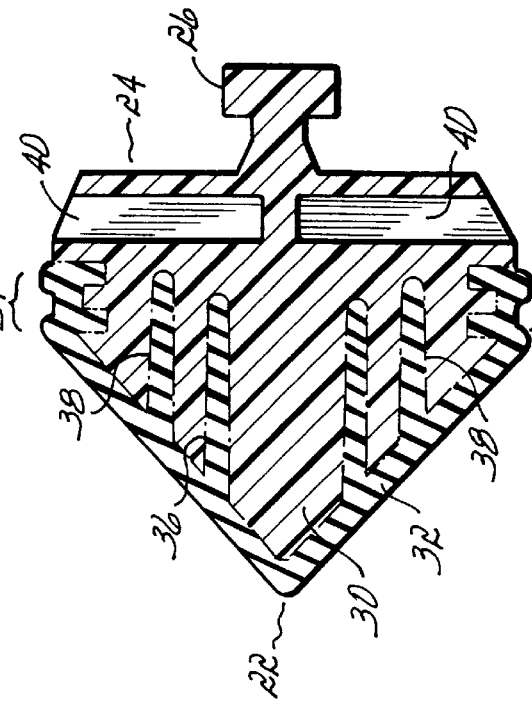

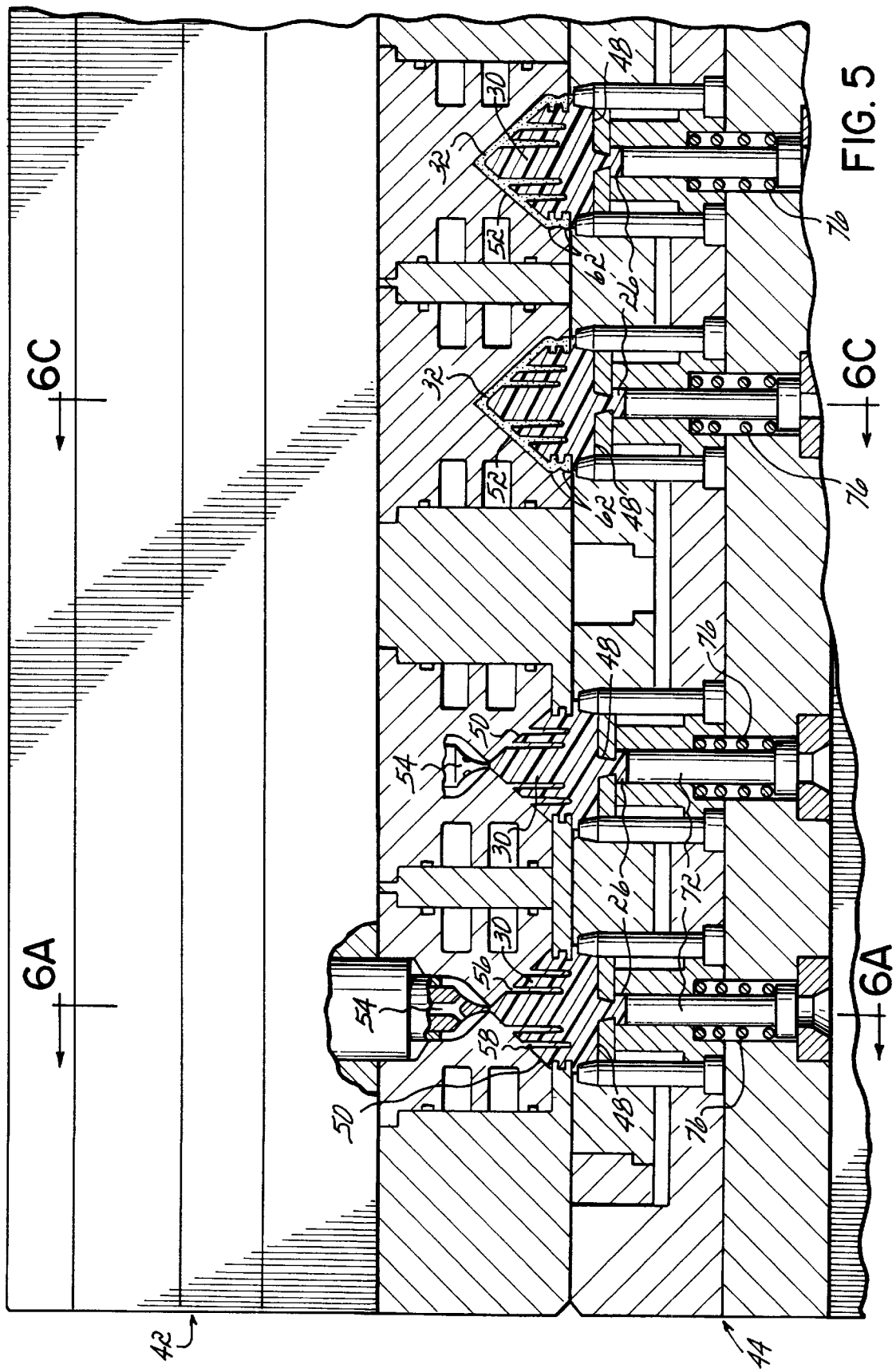

TWO-SHOT MOLDED PLUNGER

FIELD OF THE INVENTION

The present invention generally relates to plungers used in syringes to vary a syringe's volume, thereby introducing or extracting fluid from human and animal bodies.

BACKGROUND OF THE INVENTION

Two-part molded plungers are available to drive and draw fluid through syringes. These plungers are made by fitting a molded soft rubber cover over a separately molded hard plastic core. The rubber cover is typically assembled by hand over the hard plastic core to form the completed plunger. When the plunger is inserted into a syringe, the soft rubber cover creates a seal with the inner circumference of the syringe so that fluid may drawn into or driven out of the syringe. The hard plastic core provides support for the rubber cover to prevent excessive deformation and possible leakage.

Typically, that portion of the hard plastic core which supports the rubber cover against fluid pressure, must have a smooth exterior profile conforming to the profile of the rubber cover. This is necessary in order for the hard plastic core to support the rubber cover against fluid pressure generated when the plunger is driven into the syringe. Otherwise, the rubber cover would extrude into voids or depressions in the hard plastic core, weakening or damaging the rubber cover.

Several problems have plagued prior art two-part plungers. First, hand assembly of the two parts of the plunger is expensive and time-consuming. Second, because the portion of the hard plastic core which supports the rubber cover against fluid pressure must have a smooth exterior profile, in some applications there are regions of the hard plastic core including large quantities of solid plastic. These large regions of molten plastic are difficult to adequately cool and cure in a conventional injection molding process, leading to delay in manufacturing and/or quality variations as a result of some cores being removed from the mold before the plastic forming the core is adequately cured.

It would be desirable to provide a plunger that can be manufactured by a fully automated process, in which there is reduced potential for manufacturing delay and quality variation resulting from regions of uncured plastic.

SUMMARY OF THE INVENTION

It is therefore an object of the present invention to provide a syringe plunger that is not assembled from a separate soft rubber cover and a separate hard plastic core into a final product, but rather is injection molded using a two-shot process, so that the plunger emerges from the mold as a complete finished product.

A further object is to manufacture a syringe plunger which can be readily cooled and cured in a conventional injection molding process.

In accordance with the invention, a two-shot mold is used to facilitate the manufacture of this invention. Using a two-shot mold, the plastic forming the plunger's hard inner core is first injected into a suitably formed mold. Once cured, the hard plastic core is placed into a second mold and a second molding is performed in which rubber is injected over the hard plastic core, forming a rubber exterior surface for the plunger. The second overmolding of rubber occurs within a reasonable time subsequent to the first molding of the hard plastic core, so that the rubber tends to molecularly bond to the underlying hard plastic core and form a single unit.

In the disclosed specific embodiment, the two steps of the molding process occur in parallel; that is, while hard plastic is injected into one mold to form what will become the hard plastic core, rubber is injected into a second mold holding a previously molded core to form a soft rubber exterior.

The core of this two-shot molded plunger is shaped so that it will cure rapidly, reducing warping when the core is subjected to the second injection that forms the soft rubber exterior. This is accomplished by molding the core to define at least one cavity in the distal surface of the core (i.e., that surface of the core which will be overmolded with soft rubber, and is adjacent to fluid in the interior of the syringe), thereby increasing the core's surface area and reducing the core's volume. The increased surface area and diminished volume of the core facilitates rapid cooling of the hard plastic core so that the plunger may be finished more quickly, thereby reducing manufacturing costs, and also reduces the likelihood for quality variation caused by deformation of the hard plastic core due to inadequate curing.

Thus, the two-shot molded plunger and manufacturing process in accordance with the present invention reduces human labor involved plunger manufacturing, and reduces costs, while also reducing the opportunity for manufacturing defects caused by human assembly and/or inadequate cooling.

These and other objectives and advantages of the present invention will become more readily apparent to those of ordinary skill in the art upon further review of the following detailed description of the preferred embodiment taken in conjunction with the accompanying drawings.

BRIEF DESCRIPTION OF THE DRAWINGS

FIG. 1 illustrates a syringe and plunger in accordance with principles of the present invention;

FIG. 2 is perspective view of a plunger in accordance with principles of the present invention, partially cut away to show internal structures of the plunger core and rubber exterior;

FIG. 3 is a cross-sectional view of the plunger of FIG. 2 taken along lines 3—3;

FIG. 5 is a cross-sectional view of the molding apparatus of FIG. 4 taken along lines 5—5;

DETAILED DESCRIPTION OF SPECIFIC EMBODIMENTS

Figure 4:
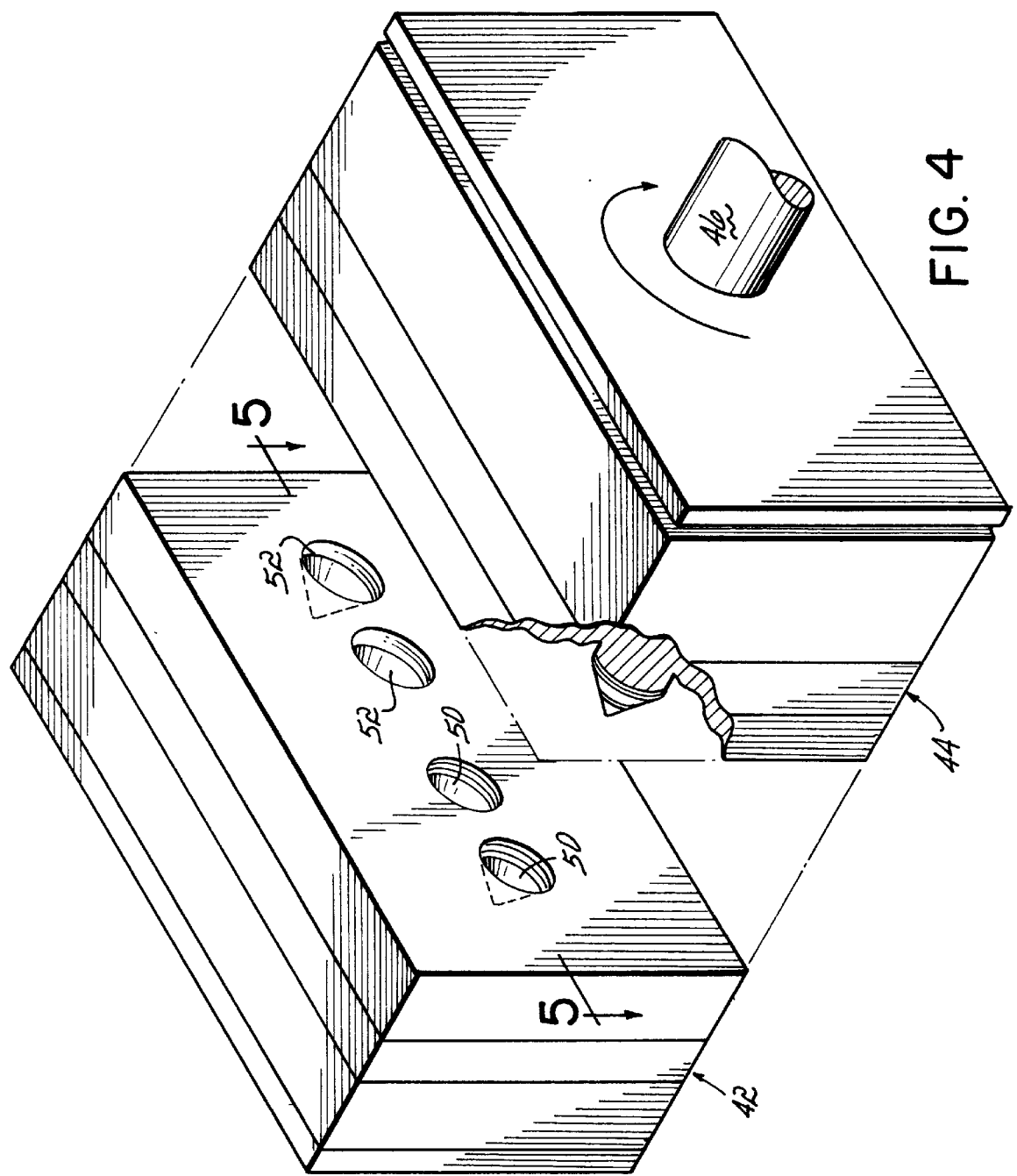
FIG. 4 is schematic perspective view of a molding apparatus for molding the plunger of FIG. 3.

Referring to FIG. 1, a syringe 10 in accordance with principles of the present invention includes a cylindrical body 12, advantageously formed of translucent plastic material, a narrow discharge end 14 through which fluid may be drawn or injected, and a flange 16 for connecting the syringe to an injector. Mounted inside of syringe 10 is a plunger 20 which seals against the cylindrical internal walls of body 12 and may be moved inside of body 12 to extract or inject fluid through discharge end 14. A distal end 22 of plunger 20 has a soft rubber exterior suitable for forming a seal with the cylindrical internal walls of syringe body 12. Proximal end 24 of plunger 20 has a hard plastic surface for engagement to a plunger drive ram for moving plunger 20 into or out of syringe body 12. A mushroom-shaped button 26 extends from the proximal end 24 of plunger 20 for engagement to jaws or other attachment devices on the plunger drive ram.

Referring now to FIGS. 2 and 3, the two-shot overmolded structure of plunger 20 can be understood. Plunger 20 comprises a hard plastic core 30 overmolded on its distal end with an exterior 32 of rubber. Notably, the overmolded rubber exterior 32 does not completely envelop hard plastic core 30, but rather only envelops the distal end 22 of plunger 20, including that portion 31 of the periphery of plunger 20 which forms a seal with the inner cylindrical wall of syringe body 12. At the proximal end of plunger 20, hard plastic core 30 is exposed. Button 26, therefore, is formed in hard plastic core 30, as are other structures on the proximal end of plunger 20, so that these areas are structurally strong and easily grasped by a plunger drive ram.

Also notable in FIGS. 2 and 3, is that hard plastic core 30 has annular cavities 36 and 38 formed therein. Cavities 36 and 38 are enveloped by rubber exterior 32, and substantially filled with rubber in the completed plunger. As will be elaborated below, the presence of cavities 36 and 38 in hard plastic core 30 reduces the volume of hard plastic core 30 and increases its surface area, thus facilitating cooling of core 30 during the molding process. Additional cavities 40 are formed in the proximal end of hard plastic core 30 for similar reasons (and to reduce the total volume of plastic consumed in manufacturing plunger 20).

Referring now to the schematic FIG. 4, a manufacturing process for forming plungers such as plunger 20 will be understood. A molding apparatus includes a first section 42 and a second section 44. Sections 42 and 44 may be pressed together to form molds for forming cores such as 30 (FIGS. 2 and 3) and overmolding rubber exteriors such as 32 (FIGS. 2 and 3). Sections 42 and 44 may also be separated, as shown in FIG. 4, to eject molded plungers and to realign mold halves, as described below. Section 42 includes mold halves 50 and 52, shown schematically on FIG. 4; these mold halves mate with mold halves formed in section 44 to form complete molds for forming cores and rubber exteriors for plungers. (As used herein, "mold half" refers to any portion of a mold which can be mated with one or more other mold portions to form a complete mold, and does not imply that the "mold half" is matable with only one other mold portion or that the "mold half" forms half of the complete mold, as measured by volume or otherwise.)

As seen in FIG. 4, section 44 is rotatable relative to section 42, e.g. on a shaft 46, to provide separate alignments of mold halves in section 44 and mold halves in section 42.

Referring now to FIGS. 5, details of the mold halves in sections 42 and 44 can be understood. Specifically, section 42 includes two mold halves 50 which provide the surface outline of the distal surface of a hard plastic core 30 of a plunger. Notably, mold halves 50 include annular projections 56 and 58 which define the exterior surfaces of cavities 36 and 38 of the hard plastic core 30 (FIGS. 2 and 3). As noted above, projections 56 and 58 increase the surface area of the core 30 while simultaneously reducing its volume, facilitating cooling of the core subsequent to molding, and thereby decreasing the manufacturing time while increasing quality.

FIG. 5 also shows valve structures such as 54 for controlling the injection of molten plastic into mold halves 50. The molten plastic supplied to mold halves 50 cures to a hard, structural plastic material, suitable for forming a structural core for plunger 20.

Figure 6A:
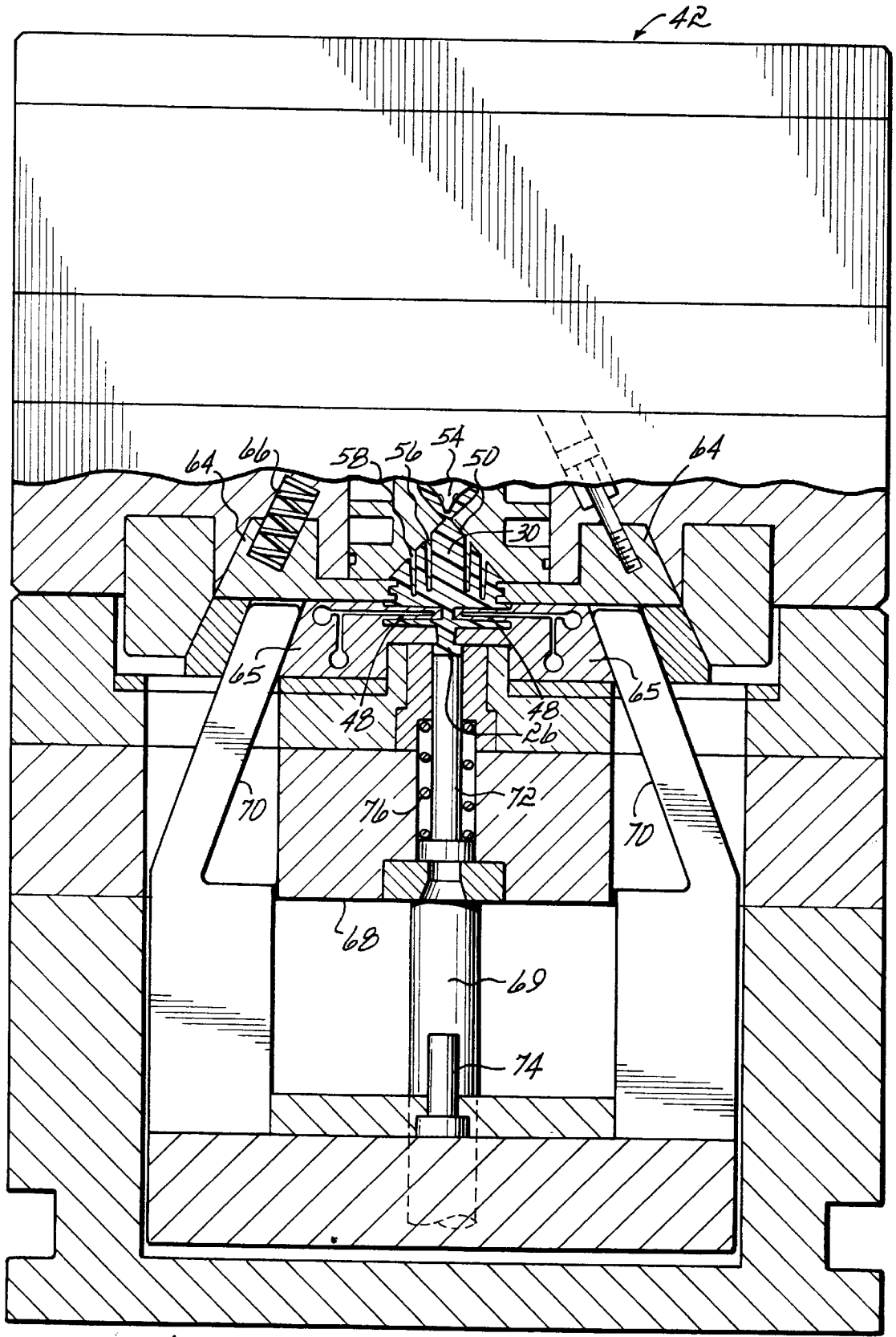
FIGS. 6A and 6B are cross-sectional views of the molding apparatus of FIGS. 4 and 5 taken along lines 6A—6A in FIG. 5, showing the molding of a plunger core using first and second mold halves.

When sections 42 and 44 are pressed together, mold halves 50 mate to mold halves 48 in section 44 to form complete molds for forming hard plastic cores 30. Mold halves 48 in section 44 define the exterior surfaces of the proximal end of hard plastic cores 30. Notable features of mold halves 48 include a region above pin 72 for forming button 26. Further, mold halves 48 include pins 60 (see FIG. 6A) which define cavities 40 in the proximal surface of plunger 20. The manner in which pins 60 interact with a plunger to facilitate removal of a plunger from mold halves 48 will be discussed below in connection with FIGS. 6A and 6D.

Section 42 further includes two mold halves 52 forming cavities for overmolding rubber exteriors 32 on previously-formed plunger cores 30. Mold halves 52 have a generally conical shape, with features such as annular bumps 62 for shaping the sealing surfaces 31 of the rubber exterior 32 of plungers. Molten rubber is injected into mold half 52 through an inlet, not shown in the Figs., which advantageously may be positioned within annular bumps 62 or elsewhere in the mold. As can be seen in FIG. 5, the soft rubber overmold covers 32 the entire distal end 22 of the plunger core 30, producing a smooth rubber surface for sealing the interior of the syringe and driving fluid in the syringe. Notably, as seen in FIG. 5, rubber injected into mold half 52 fills or substantially fills cavities 56 and 58 in the hard plastic plunger core 30, resulting in a void-free plunger.

The operation of the apparatus of FIG. 5 can be described in greater detail with reference to FIGS. 6A–6D. Specifically, referring to FIG. 6A, in a first step, sections 42 and 44 are pressed together such that a mold half 48 in section 44 is pressed against a mold half 50 in section 42, producing a mold shaped in the form of a plunger core 30. Molten plastic, which will cure to a hard molecular structure, is then injected into this mold to form the plunger core 30.

Figure 6B:
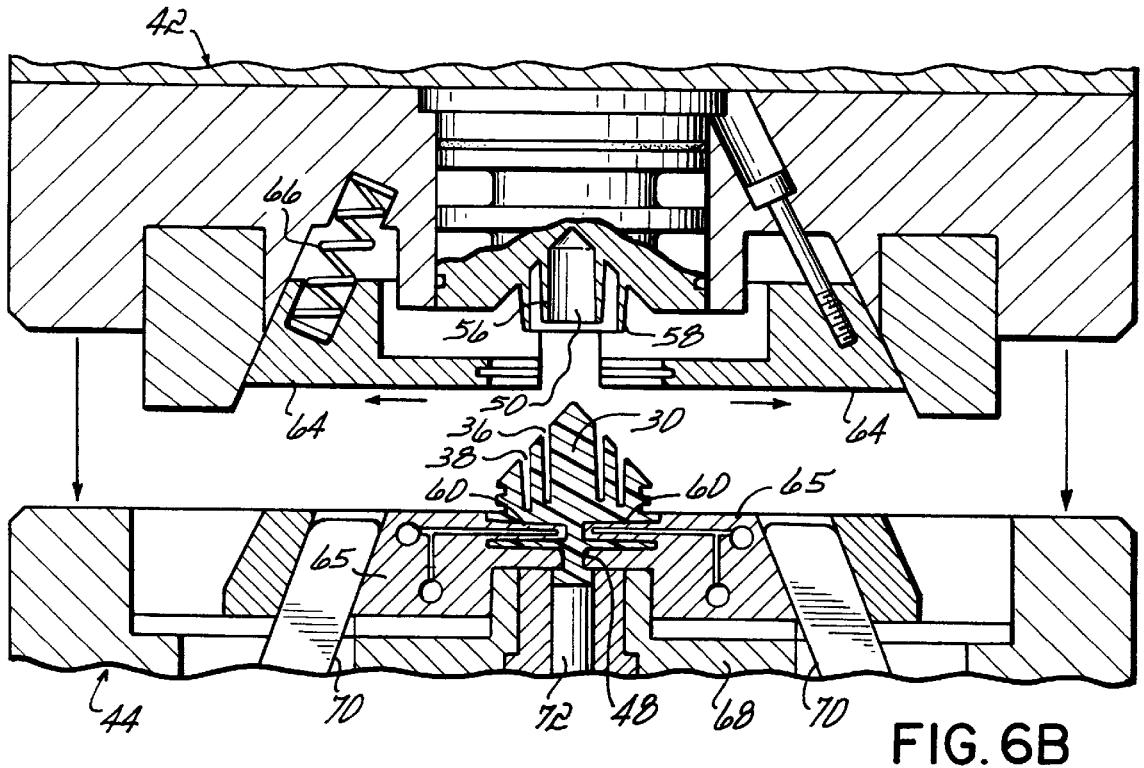

In the second step, sections 44 and 42 are drawn apart, as seen in FIG. 6B. As sections 42 and 44 are drawn apart, sliders 64, which are actuated by a spring 66, slide downward and outward away from section 42, releasing the cooling plunger core 30 from sliders 64 so that it may be extracted from mold half 50. At the same time, plunger core 30 remains held in place by mold half 48 in section 44, and in particular by pins 60 which extend into cavities 40 in the proximal end of plunger core 30.

Figure 6C:
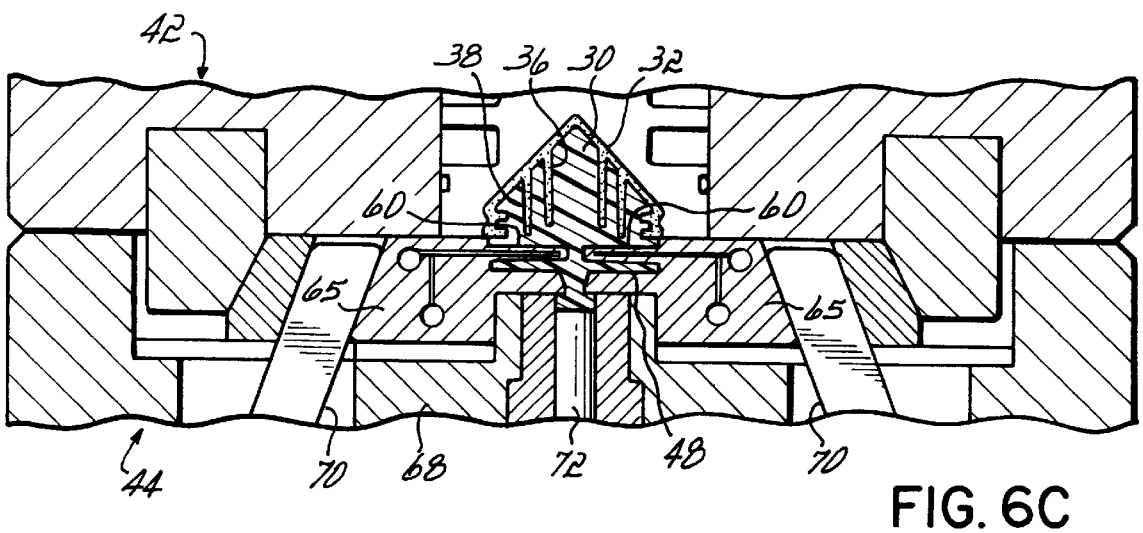
FIGS. 6C and 6D are cross-sectional views of the molding apparatus of FIGS. 4 and 5 taken along lines 6C—6C in FIG. 5, showing the overmolding of a rubber exterior on a plunger core using first and third mold halves.
Figure 6D:
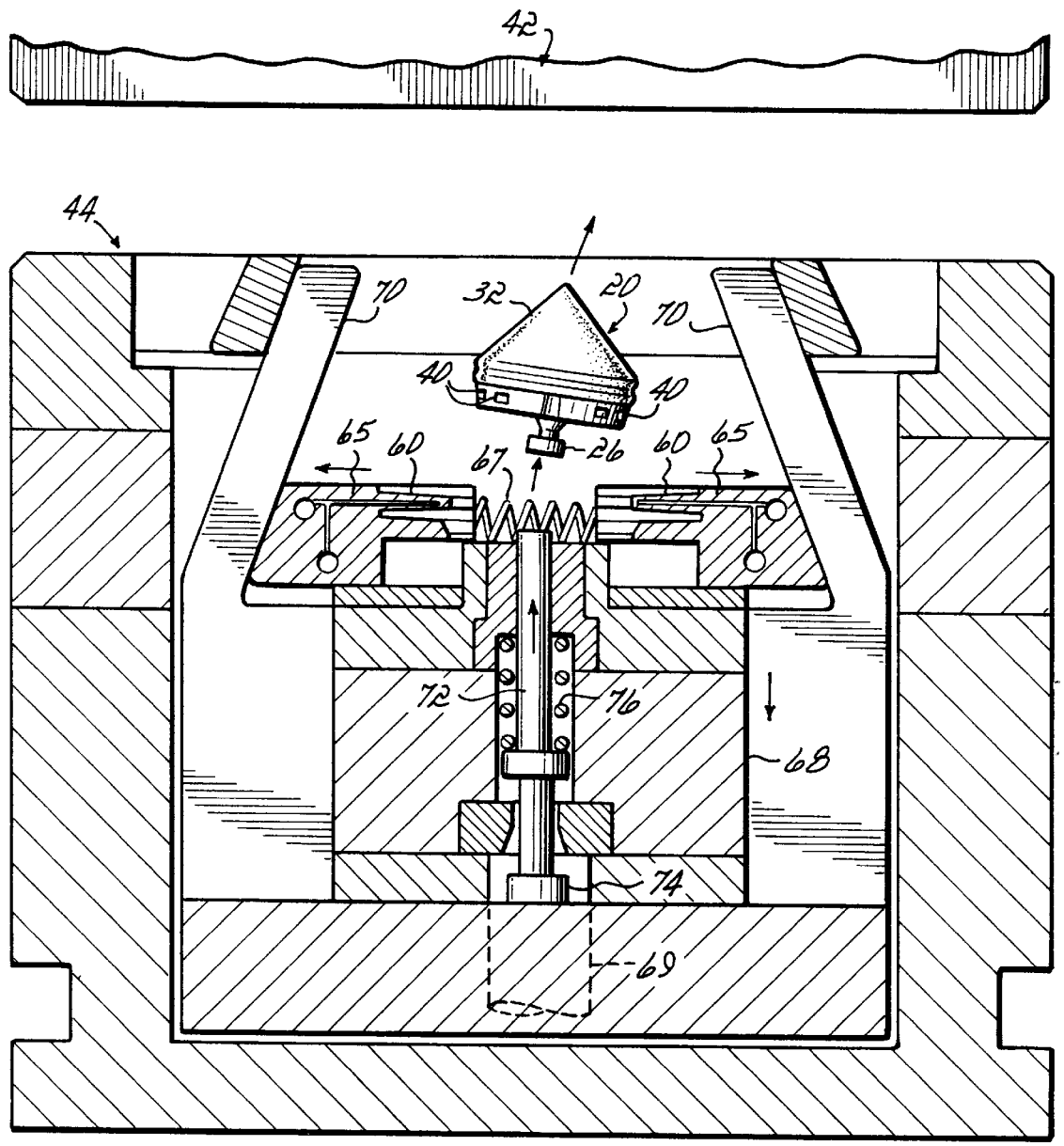

To prepare for the third step, sections 44 and 42 are rotated 180 degrees relative to each other, e.g., by rotating section 44 on shaft 46 as shown in FIG. 4. Doing so brings mold half 48 in section 44 into registration with a mold half 52 in section 42. Sections 42 and 44 and then pressed together to form a second mold shaped to form the exterior of the plunger, as seen in FIG. 6C. During this rotation, and the re-engagement of sections 42 and 44, the plunger core 30 formed in the first step remains affixed in mold half 48, specifically, pins 60 extend into cavities 40 in the proximal end of the plunger core 30 to hold the core in place. Accordingly, when the second mold is formed from mold half 48 and mold half 52, plunger core 30 is positioned inside of the second mold in the appropriate position for overmolding of rubber.

The hard plastic core 30 begins cooling and curing immediately after injection of molten plastic ceases. Although the overmolding of rubber may be done after the core is completely cool, advantageously, overmolding is performed while core 30 is still curing and cooling. Accordingly, core 30 is rapidly removed from the first mold 42 and placed into the second mold 44, and rubber 32 is overmolded on core 30. If the core 30 is moved into the second mold while it is still cooling, the rubber injected in the second overmold will molecularly bond with the as-yet uncured plastic of the core 30, forming a secure bond between the soft rubber exterior 32 and the hard plastic interior 30. Accordingly, the separation, rotation, and re-engagement of sections 42 and 44 begins as soon as the core 30 has cooled to a sufficient extent to be self-supporting when mold half 50 is removed.

In the third step, rubber 32 is injected into the second mold 44 formed of mold half 48 and mold half 52, producing a rubber exterior 32 on the plunger core 30 as seen in FIG. 6C. As noted above, the rubber injected during this step not only covers the distal end of the plunger core 30 and forms sealing surfaces 31 around the perimeter of the plunger, the rubber overmold also substantially fills cavities 36 and 38 in the plunger core 30 so the resulting structure is a substantially solid plunger.

In the final step, as the rubber 32 overmold is cooling, sections 42 and 44 are again separated, removing the completed plunger 20 from mold half 52 in section 42. At the same time, the completed plunger is ejected by motions which become apparent by comparing FIGS. 6A and 6C to FIG. 6D. Specifically, block 68, which is pressed to the outer surface of section 44 by, for example, a shaft 69, is withdrawn from the surface of section 44, causing the completed plunger 20 to move downward from the outer surface of section 44. Simultaneously, sliders 65, which are spring-actuated, for example by a spring 67, slide downwardly and outwardly along cam surfaces 70, withdrawing pins 60 from cavities 40 in the completed plunger. Ultimately, when block 68 reaches its innermost position, ejection pin 74 comes into contact with shaft 72, and actuates shaft 72 upward against the force of spring 76. The button 26 of the completed plunger is formed by the upper surface of shaft 72 during the molding process; accordingly, actuation of shaft 72 caused by ejection pin 74 ejects the completed plunger 20 from section 44 and into a suitable storage bin, ready for insertion into a syringe.

It will be noted that, from the construction of the molding apparatus, particularly as seen in FIGS. 4 and 5, the apparatus performs the first and second moldings in parallel. In particular, whenever sections 42 and 44 are pressed together, two plunger cores are formed on a first side of the apparatus using mold halves 50, while simultaneously two previously-formed plunger cores are overmolded with rubber on a second side of the apparatus using mold halves 52. When sections 42 and 44 are subsequently separated, the two completed plungers formed in the second side of the apparatus using mold halves 52 are ejected, sections 42 and 44 are rotated relative to each other, and sections 42 and 44 are again pressed together to place the two cores just formed with mold halves 50, into mold halves 52, and also to join the empty mold halves 48 from which finished plungers were just ejected, with mold halves 52, ready to form new cores.

While the present invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. For example, the apparatus for forming plungers described here might be altered in various ways, e.g., by forming only one plunger core and overmold at a time, or by forming more than two cores and two overmolded exteriors simultaneously. The mold halves may mate in different ways and their relative motions between molding phases may be substantially different without changing in substance the manner in which a plunger is molded. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A syringe plunger comprising:
   a hard core, and
   a soft exterior molded over said hard core by a two-shot process while said hard core is cooling and incompletely cured,
   wherein said soft exterior is molecularly bonded to said hard core as a consequence of said two-shot process.

2. The syringe plunger of claim 1 wherein said hard core is of plastic.

3. The syringe plunger of claim 1 wherein said soft exterior is of rubber.

4. The syringe plunger of claim 1 wherein said hard core defines at least one cavity in its body.

5. The syringe plunger of claim 4 wherein said cavity is formed in a surface of said hard core covered by said soft exterior.

6. The syringe plunger of claim 1 wherein at least one exposed surface of said hard core is not covered by said soft exterior.

7. The syringe plunger of claim 6 wherein said hard core further comprises at least one button extending from said exposed surface.

8. The syringe plunger of claim 7 wherein said button extends from said exposed surface parallel to a longitudinal axis of said plunger.

9. A syringe comprising:
   a hollow cylindrical body including an open rearward end and a closed open end having a discharge opening, and
   a plunger inserted in said open rearward end, the plunger comprising a hard core and a soft exterior molded over said hard core by a two-shot process while said hard core is cooling and incompletely cured, wherein said soft exterior is molecularly bonded to said hard core as a consequence of said two-shot process.

10. The syringe of claim 9 wherein said hard core of said plunger is of plastic.

11. The syringe of claim 9 wherein said soft exterior of said plunger is of rubber.

12. The syringe of claim 9 wherein said hard core of said plunger defines at least one cavity in its body.

13. The syringe of claim 12 wherein said cavity is formed in a surface of said hard core of said plunger covered by said soft exterior.

14. The syringe of claim 9 wherein at least one exposed surface of said hard core of said plunger is not covered by said soft exterior.

15. The syringe of claim 14 wherein said hard core of said plunger further comprises at least one button extending from said exposed surface.

16. The syringe of claim 15 wherein said button extends from said exposed surface parallel to a longitudinal axis of said plunger.

* * * * *

UNITED STATES PATENT AND TRADEMARK OFFICE
CERTIFICATE OF CORRECTION

PATENT NO. : 5,902,276
DATED : May 11, 1999
INVENTOR(S) : David Namey, Jr.

It is certified that error appears in the above-indentified patent and that said Letters Patent is hereby corrected as shown below:

Column 1, line 15 reads "many drawn" and should read --may be drawn--.

Column 3, line 54 reads "Figs. 5" and should read --Fig. 5--.

Column 4, line 54 reads "and then" and should read --are then--.

Signed and Sealed this

Eighth Day of February, 2000

Attest:

Q. TODD DICKINSON

*Attesting Officer*

*Commissioner of Patents and Trademarks*